United States Patent [19]

Sipos

[11] Patent Number: 4,460,564

[45] Date of Patent: Jul. 17, 1984

[54] ANTICARIES COMPOSITIONS

[75] Inventor: Tibor Sipos, Lebanon, N.J.

[73] Assignee: Johnson & Johnson Products Inc., New Brunswick, N.J.

[21] Appl. No.: 442,697

[22] Filed: Nov. 18, 1982

[51] Int. Cl.³ .......................... A61K 7/16; A61K 7/18
[52] U.S. Cl. ........................................ 424/52; 424/49
[58] Field of Search .................................... 424/49–58

[56] References Cited

U.S. PATENT DOCUMENTS

| | | | |
|---|---|---|---|
| 4,138,477 | 2/1979 | Gaffar | 424/52 |
| 4,243,658 | 1/1981 | Chang | 424/49 |
| 4,304,766 | 12/1981 | Chang | 424/52 |
| 4,307,077 | 12/1981 | Buck | 424/56 |
| 4,307,078 | 12/1981 | Buck | 424/56 |
| 4,314,991 | 2/1982 | Sipos | 424/56 |
| 4,360,512 | 11/1982 | Vidra | 424/56 |
| 4,360,513 | 11/1982 | Buck | 424/56 |
| 4,360,514 | 11/1982 | Buck | 424/56 |
| 4,360,515 | 11/1982 | Buck | 424/56 |
| 4,362,712 | 12/1982 | Buck | 424/49 |
| 4,364,972 | 12/1982 | Sipos et al. | 424/56 |

OTHER PUBLICATIONS

A.D.A. Accepted Dental Therapeutics, 38th Ed., Sep. 1979, American Dental Assn., Chicago, IL, pp. 316-338, "Fluoride Compounds".

Primary Examiner—Shep K. Rose
Attorney, Agent, or Firm—Steven P. Berman

[57] ABSTRACT

Compositions providing improved protection against dental caries consisting of a pharmaceutically acceptable fluoride compound and a pharmaceutically acceptable sulfonated alkylnaphthalene in a suitable vehicle are described.

6 Claims, No Drawings

ANTICARIES COMPOSITIONS

BACKGROUND OF THE INVENTION

The present invention relates to compositions for preventing dental caries. More particularly, it relates to fluoride-containing compositions that have enhanced activity in preventing dental caries.

The use of soluble fluoride salts, such as stannous fluoride and sodium fluoride, to reduce the incidence of dental caries in the general population is a well-known and ongoing endeavor. The administration of these fluoride compounds takes many forms, including the fluoridation of drinking water, professional treatment by dentists and incorporation in oral hygiene compositions such as dentifrices and mouthrinses.

Notwithstanding the widespread acceptance of such compositions, there is an ongoing search for more effective compositions and, therefore, there is a need to enhance the fluoride activity of various fluoride compounds by the addition of other compounds. In copending U.S. patent application Ser. No. 303,284, filed Sept. 17, 1981 now U.S. Pat. No. 4,396,599, there is suggested the use of various zinc salts to enhance the activity of fluoride compounds.

One of the objects of the present invention is to provide improved compositions for preventing dental caries.

Another object of this invention is to provide anticaries compositions comprising one or more anticaries compounds in combination with a compound which enhances the anticaries activity of said anticaries compounds.

These and other objects of the invention will become apparent from the foregoing description.

SUMMARY OF THE INVENTION

In accordance with the present invention, there are provided compositions useful in preventing dental caries comprising (a) at least one fluoride salt and (b) a specific sulfonated alkylnaphthalene.

The enhancing effect on the anticaries properties of the compositions of the present invention is most notable when the fluoride salt is employed with the sulfonated alkylnaphthalene within specific concentrations and the compositions of the invention can be employed in various oral hygiene products.

DETAILED DESCRIPTION OF THE INVENTION

It has now been discovered that the rate of development of dental caries, as characterized by proximal, smooth surface, pit and fissure caries, can be prevented or substantially retarded by the daily application to the teeth of a composition comprising a pharmaceutically acceptable oral hygiene vehicle containing an effective concentration to prevent or inhibit dental caries of a pharmaceutically acceptable fluoride salt and a pharmaceutically acceptable sulfonated alkylnaphthalene.

Typical pharmaceutically acceptable fluoride compounds that are suitable for use in the compositions of this invention include sodium fluoride, potassium fluoride, lithium fluoride, aluminum fluoride, zinc fluoride, stannous fluoride, sodium monofluorophosphate, acidulated phosphate fluoride, ammonium fluoride, ammonium bifluoride and amine fluoride.

The sulfonated alkylnaphthalenes useful in the compositions of the present invention are selected from the group consisting of:
monoalkylnaphthalene monosulfonate salts of structure (A),

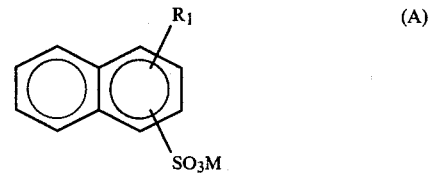

dialkylnaphthalene monosulfonate salts of structure (B),

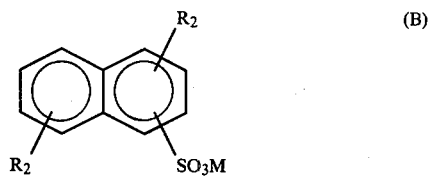

monoalkylnaphthalene disulfonate salts of structure (C),

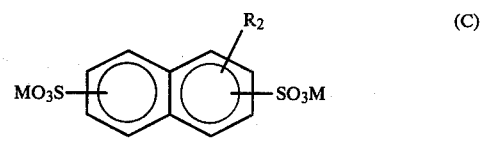

and dialkylnaphthalene disulfonate salts of structure (D),

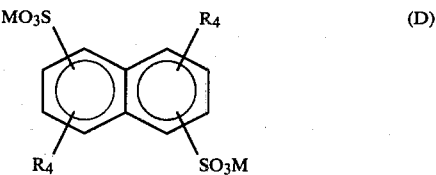

wherein $R_1$ is a linear or branched alkyl having 8 to 20 carbon atoms, $R_2$ is a linear or branched alkyl having 8 to 20 carbon atoms, $R_3$ is a linear or branched alkyl having 8 to 20 carbon atoms, $R_4$ is a linear or branched alkyl having 8 to 20 carbon atoms, and M is selected from the group consisting of lithium, sodium, potassium, calcium, magnesium, zinc, copper, aluminum, ammonium and the substituted ammonium ions derived from pharmaceutically acceptable organic amines.

Certain of the alkylnaphthalene sulfonates useful in the practice of this invention are items of commerce. These include the following sulfonic acids and salts sold by King Industries, Inc., Norwalk, Conn.: (a) Dinonylnaphthalene sulfonic acid, available as "Synex TM Liquid Ion Exchange Reagents"-"DN-040" "DN-051", and "DN-052"; (b) Sodium dinonylnaphthalene sulfonate, as "Synex TM DN-150"; (c) Dinonylnaphthalene disulfonic acid, as "Nacure TM 155:DMEA Salt"; (d) Sodium dinonylnaphthalene disulfonate; (e) Didodecylnaphthalene sulfonic acid, as "Synex TM DD-040" and "DD-052".

The alkylnaphthalene sulfonates of this invention (structures (A) through (D)) can be synthesized by a three-step process consisting of (1) Friedel-Crafts alkylation of naphthalene to afford either the mono- or dialkylnaphthalene, (2) Aromatic sulfonation to either the mono- or disulfonic acid derivative, and (3) Conversion of the sulfonic acid group to the metal, ammonium, or substituted ammonium salt. The general sequence for preparation of the sulfonic acid intermediates is shown schematically in equation (1)

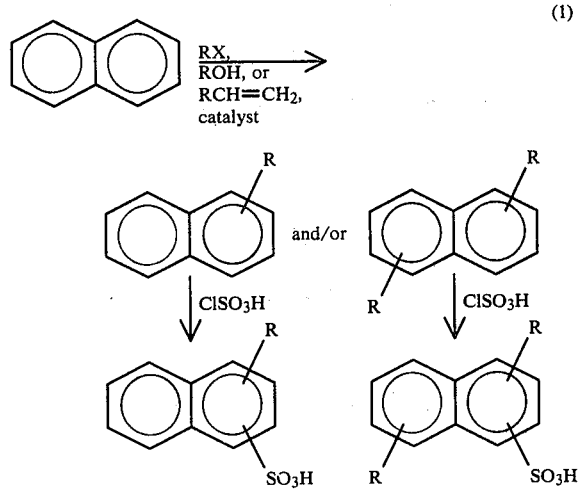

(1)

The Friedel-Crafts method for the alkylation of naphthalene with alkyl halides, alcohols, or olefins to the corresponding alkylnaphthalenes has been extensively described in the literature and reviewed e.g. by C. C. Price in "Organic Reactions", Volume 3, Chapter 1, pages 1–82, John Wiley & Sons, Inc., 1946. The alkylation reaction, catalyzed by materials such as aluminum chloride, antimony pentachloride, ferric chloride, stannic chloride, zinc chloride, hydrogen fluoride, sulfuric acid, and phosphoric acid, must be carefully controlled to achieve the degree of alkylation required and minimize formation of undesired polyalkylation and rearrangement products (C. C. Price, supra). Rearrangement of the alkyl group introduced by the Friedel-Crafts alkylation reaction is a common occurrence, so that alkylations with linear alkyl halides, alcohols, and olefins often result in the formation of a mixture of linear and branched alkyl-substituted aromatic compounds. The position of substitution of the alkyl groups on the aromatic ring is dependent on the reaction conditions and type of catalyst utilized.

The commonly available monoalkylnaphthalene and dialkylnaphthalene compounds that are useful as intermediates for the preparation of the sulfonated derivatives of this invention consist largely of mixed linear and branched alkylated naphthalenes, wherein the distribution of the alkyl groups on the aromatic ring is generally random.

Naphthalene substituted with linear alkyl groups can be synthesized in two steps: (1) Friedel-Crafts acylation of naphthalene with an acyl chloride, RCOCl (where R is a linear alkyl group), to an acylated naphthalene, followed by (2) Clemmenson reduction or Wolff-Kishner reduction of the carbonyl group. These reactions, shown generally in equation (2), are well known in the literature and are discussed in textbooks, such as that by R. T. Morrison and R. N. Boyd entitled "Organic Chemistry," Third Edition, Chapters 12, 19, and 30, Allyn and Bacon, Inc., 1973.

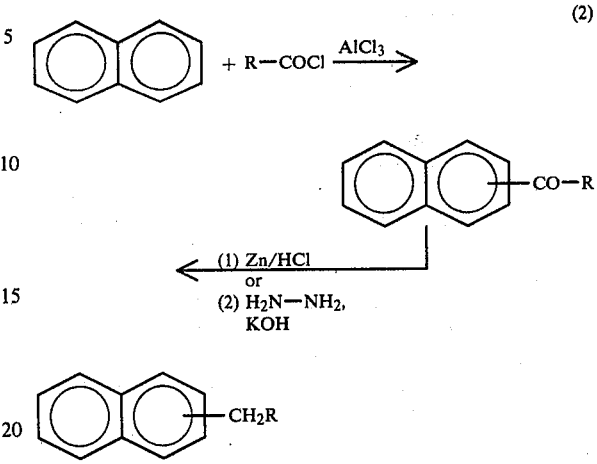

(2)

where R = linear alkyl

Sulfonation of the monoalkylnaphthalenes and dialkylnaphthalenes to the sulfonic acid precursors of the sulfonated salts having structures (A)–(D) can be effected with such reagents as concentrated sulfuric acid, oleum, chlorosulfonic acid and liquid sulfur trioxide. The sulfonations are generally effected in inert solvents, such as methylene chloride, chloroform, and 1,2-dichloroethane; at temperatures of 40° C. or below.

Common conditions for sulfonation of naphthalene and various alkylnaphthalenes can also be found in the review by C. M. Suter, "Organic Reactions", Volume 3, Chapter 4, John Wiley & Sons, Inc., 1946. For synthesis of the desired monosulfonated and disulfonated alkylnaphthalenes of this invention, careful control of the stoichiometry of the sulfonation reaction is necessary. Despite the various precautions taken, it is often impossible to avoid formation of mixed sulfonated products. Isolation and purification of the desired mono- or disulfonated alkylnaphthalenes is generally effected by fractional crystallization, fractional solubilization, or column chromatography on silica gel, techniques which are preferably done on the salt forms of the sulfonic acid derivatives.

The position of substitution of the sulfonate groups on the aromatic rings of the alkylnaphthalene compounds is generally not known with certainty and, in any event, is not considered important in the practice of this invention. However, structure characterization, determination of the number of sulfonic acid groups introduced, and purity of the sulfonate salt derivatives or their sulfonic acid precursors can be determined by a number of known methods: (1) NMR and IR spectroscopic analysis, (2) acidimetric assays (on the sulfonic acid derivatives), (3) metal salt analysis via atomic absorption, and (4) elemental analysis for carbon, hydrogen and sulfur.

The alkali metal salts of the sulfonated alkylnaphthalenes are conveniently prepared by neutralization of a water or alcohol solution of the sulfonic acid derivative with alkali metal hydroxide solutions to the potentiometric endpoint. The salts are recovered by filtration, solvent stripping, or freeze drying, depending on the type of solvent used and whether the salt precipitates directly from the solvent medium. Alternatively, sulfonate salts can be prepared by addition of at least stoichiometric quantities of an alkali metal oxide, carbonate, acetate, chloride, nitrate, or sulfate to the sulfonic acid derivative. The salts either precipitate directly, or are isolated by solvent stripping.

Multivalent metal salts, such as the calcium, magnesium, zinc, copper, and aluminum salts, of the sulfonated products are prepared by methods similar to those described above. In an alternate procedure, multivalent metal salts can be prepared by an ion-exchange reaction between the multivalent ion and either the free sulfonic acid or an alkali metal sulfonate derivative. Ammonium salts of the sulfonic acid derivatives can be prepared by direct addition of ammonia or a primary, secondary, or tertiary organic amine.

In connection with the above compositions, the fluoride ion concentration should be from about 0.005 to 2.00% by weight of the total composition, preferably from about 0.01 to 1.00%. The concentration of the sulfonated alkylnaphthalene should be at least 0.0001% by weight of the total composition, preferably from about 0.01 to 5.00% and most preferably from about 0.05 to 3.00%. In concentrate formulations, the sulfonated alkylnaphthalene may have a concentration as high as 80% by weight of the total composition.

Suitable pharmaceutically acceptable oral hygiene vehicles, that may be used alone or in any compatible combination, include glycerol, water, ethanol, polyethylene glycol, propylene glycol and sorbitol. Alternatively, any pharmaceutically acceptable vehicle which is compatible with the sulfonated polymeric material and fluoride salts used may be employed.

The compositions of this invention may be in the form of a mouthrinse, dentifrice, gel, powder, solution, varnish, lozenge, chewing gum, slow release device or concentrate to be diluted or other form suitable for oral application. Any pharmaceutically acceptable materials, such as those ordinarily used in such oral compositions, that are compatible may be employed in the compositions of this invention.

In accordance with the present invention, the compositions are applied to the teeth with an appliance, e.g., toothbrush, swab, mechanical cleansing devices, impregnated dental floss or the like, by gently brushing the teeth at least one daily, more preferably twice daily.

Specific embodiments of the anticaries compositions prepared in accordance with the present invention are illustrated by the following representative examples. It will be understood, however, that the invention is not confined to the specific limitations set forth in the individual examples, but rather to the scope of the appended claims.

EXAMPLE I

A gel dentifrice is prepared as follows: the Pluronic F-127 surface active agent is dissolved in 50 ml. of deionized water with continuous stirring at 70° C. The sulfonated dinonylnaphthalene is then added with stirring until dissolved. The resultant solution is then cooled to 50° C. and the sodium fluoride, glycerol, sorbitol, sodium benzoate, sweetener, flavoring, dye and silicone dioxide are individually added. The pH of the solution is then adjusted to 5.5 to 6.0 with 1.0N HCl or 1.0N NaOH as required and deionized water is added to bring the total weight to 100 g. The solution is permitted to gel overnight at 15° C.

The resulting gel dentifrice has the following composition:

|  | % w/w |
|---|---|
| sodium fluoride | 0.22 |
| zinc salt of a sulfonated dinonylnaphthalene | 1.00 |
| silicon dioxide | 1.00 |
| Pluronic F-127 (Wyandotte Chemicals Corporation's tradename for a nonionic surface active agent prepared by the addition of ethylene oxide to polypropylene glycol) | 18.00 |
| sweetener | 0.80 |
| sodium benzoate | 0.30 |
| glycerol | 10.00 |
| sorbitol solution, 70% | 2.00 |
| flavoring | 0.80 |
| dye (0.5% aq. soln.) | 0.70 |
| deionized water | q.s. to 100 |

EXAMPLE II

An abrasive paste dentifrice is prepared as follows: the sodium fluoride, sodium benzoate, sweetener, Pluronic F87 and zinc salt of a sulfonated didodecylnaphthalene are dissolved in 25 ml. of water at 50° C. with continuous stirring. In separate vessels, the xanthan gum is mixed with the glycerol and the Natrosol 250H is mixed with the sorbitol and then each of these mixtures is added to the solution. The Zeothix 265, titanium dioxide, and hydrous silica gel are then individually added to the solution with stirring. The pH of the solution is then adjusted to 5.0 to 6.0 with 1.0N HCl or 1.0N NaOH as required and the flavoring is then added as well as enough deionized water to bring the solution to 100 g. The resultant product is mixed and placed in containers and permitted to stand at 20° C. overnight.

The resulting abrasive paste dentifrice has the following composition:

|  | % w/w |
|---|---|
| sodium fluoride | 0.22 |
| zinc salt of a sulfonated didodecylnaphthalene | 1.00 |
| sodium benzoate | 0.20 |
| sweetener | 0.50 |
| titanium dioxide | 0.50 |
| flavoring | 1.00 |
| glycerol | 10.00 |
| sorbitol soln. 70% | 12.00 |
| hydrous silica gel | 15.00 |
| Zeothix 265 | 9.00 |
| Natrosol 250H (Hercules Inc. tradename for nonionic water soluble cellulose ether) | 1.00 |
| xanthan gum | 1.00 |
| Pluronic F87 (Wyandotte Chemical Corporation's tradename for a nonionic surface active agent prepared by the addition of ethylene oxide to polypropylene glycol) | 3.00 |
| deionized water | q.s. to 100 |

EXAMPLE III

A mouthrinse solution is prepared as follows: the flavoring is dissolved in ethanol in a suitable stainless steel vessel. The Pluronic F-108, water, glycerol, sorbitol, sweetener, zinc salt of a sulfonated dinonylnaphthalene and sodium fluoride are individually added with continuous stirring. The pH is adjusted to 5.5 to 6.0 with 1.0N HCl and the entire solution is strained through a 400 mesh stainless steel screen.

The resulting mouthrinse has the following composition:

|  | % w/w |
| --- | --- |
| sodium fluoride | 0.05 |
| zinc salt of a sulfonated dinonylnaphthalene | 0.02 |
| ethanol, USP | 7.0 |
| Pluronic F108 (Wyandotte Chemical Corporation's tradename for a nonionic surface active agent prepared by the addition of ethylene oxide to polypropylene glycol) | 2.00 |
| glycerol | 10.00 |
| sorbitol soln. 70% | 10.00 |
| sweetener | 0.20 |
| flavoring | 0.20 |
| deionized water | q.s. to 100 |

EXAMPLE IV

An in vitro assay technique is utilized to demonstrate the enhancing properties of the sulfonated polymeric material on fluoride ion activity. This technique is based on the titrametric measurement of organic acids produced from sucrose by the cariogenic bacterium *S. mutans*.

A fresh cell suspension of *Streptococcus mutans* 6715, grown in Trypticase Soy Broth for 16–18 hrs. at 35° C., centrifuged and the cells then resuspended in buffer containing dithiothreitol is used in the assay system.

The cell suspension is stored under anaerobic conditions at 4° C. until used. The assay utilizes a pH-stat and the reaction is carried out under a nitrogen atmosphere at 37° C. The production of acid is monitored with the automatic addition of 0.005N potassium hydroxide solution. The cells are initially activated with glucose at pH 7.5. After the exhaustion of glucose, the pH of the reaction mixture is manually dropped to 5.5 with 0.01N HCl. Sucrose is added and after 4 minutes of acid production, the test compound is added. The rate of acid production is recorded as ml of potassium hydroxide consumed per minute to maintain a pH of 5.5. Antiacidogenic acitivity is reported as that amount of compound which reduces the acid production by a given percent as compared to a control containing no test compound. The higher the percent reduction of acid production of a composition containing the sulfonated polymeric material and fluoride ion compared to a composition containing the sulfonated polymeric material alone, the better the anticaries activity of such a composition. When the zinc salt of dinonylnaphthalene sulfonate is tested at a concentration of 0.001 as above, the following results are obtained:

| % reduction of acid production | | |
| --- | --- | --- |
| fluoride alone | compound alone | compound plus fluoride ion |
| 20 | 28 | 80 |

When the zinc salt of dinonylnaphthalene sulfonate is tested at a concentration of 0.002 as above, the following results are obtained:

| % reduction of acid production | | |
| --- | --- | --- |
| fluoride alone | compound alone | compound plus fluoride ion |
| 20 | 46 | 100 |

In addition to the preferred embodiments described herein, other embodiments, arrangements, and variations within the spirit of the invention and the scope of the appended claims will occur to those skilled in the art.

What is claimed is:

1. In a composition for preventing dental caries consisting essentially of a pharmaceutically acceptable oral hygiene vehicle containing an effective concentration to prevent caries of at least one pharmaceutically acceptable fluoride salt; the improvement which consists of including therewith a fluoride ion activating enhancing amount of a pharmaceutically acceptable sulfonated alkylnaphthalene selected from the group consisting of:

monoalkylnaphthalene monosulfonate salts of structure (A),

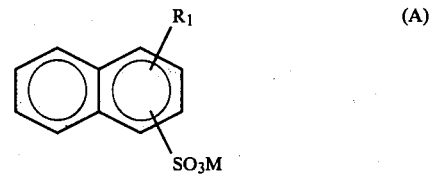

dialkylnaphthalene monosulfonate salts of structure (B),

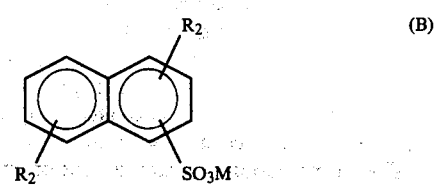

monoalkylnaphthalene disulfonate salts of structure (C),

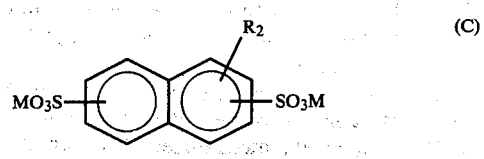

and dialkylnaphthalene disulfonate salts of structure (D),

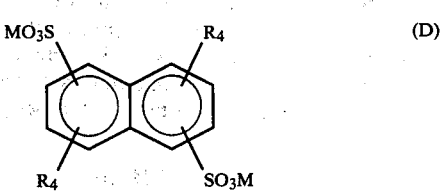

wherein $R_1$ is a linear or branched alkyl having 8 to 20 carbon atoms, $R_2$ is a linear or branched alkyl having 8 to 20 carbon atoms, $R_3$ is a linear or branched alkyl having 8 to 20 carbon atoms, $R_4$ is a linear or branched alkyl having 8 to 20 carbon atoms, and M is selected from the group consisting of lithium, sodium, potassium, calcium, magnesium, zinc, copper, aluminum, ammonium and the substituted ammonium ions derived from pharmaceutically acceptable organic amines.

2. The composition of claim 1 wherein the sulfonated alkylnaphthalene is a salt of a sulfonated dinonylnaphthalene.

3. The composition of claim 1 wherein the sulfonated alkylnaphthalene is a salt of a sulfonated didodecylnaphthalene.

4. The composition of claim 1 wherein said fluoride salt is selected from the group consisting of sodium fluoride, potassium fluoride, lithium fluoride, aluminum fluoride, zinc fluoride, stannous fluoride, sodium monofluorophosphate, acidulated phosphate fluoride, ammonium fluoride, ammonium bifluoride and amine fluoride.

5. The composition of claim 1 wherein the fluoride ion is present in a concentration of from about 0.005 to 2.00% by weight of the total composition.

6. The composition of claim 1 wherein the sulfonated alkylnaphthalene is present in an amount of from about 0.0001 to 80.00% by weight of the total composition.

* * * * *